(12) United States Patent
Lee et al.

(10) Patent No.: US 10,558,833 B2
(45) Date of Patent: Feb. 11, 2020

(54) KEY MODULE AND MOBILE TERMINAL HAVING THE SAME

(71) Applicant: LG ELECTRONICS INC., Seoul (KR)

(72) Inventors: Yongho Lee, Seoul (KR); Wonjin Choi, Seoul (KR); Minho Park, Seoul (KR); Changbai Won, Seoul (KR); Myoungku Lee, Seoul (KR); Seyun Hwang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 244 days.

(21) Appl. No.: 15/663,264

(22) Filed: Jul. 28, 2017

(65) Prior Publication Data
US 2018/0218194 A1 Aug. 2, 2018

(30) Foreign Application Priority Data

Feb. 2, 2017 (KR) ........................ 10-2017-0015109

(51) Int. Cl.
| | |
|---|---|
| *H05K 5/00* | (2006.01) |
| *G06K 9/00* | (2006.01) |
| *G07C 9/00* | (2020.01) |
| *H04N 1/00* | (2006.01) |
| *H04W 88/02* | (2009.01) |
| *A61B 5/1172* | (2016.01) |

(52) U.S. Cl.
CPC ..... *G06K 9/00013* (2013.01); *G07C 9/00158* (2013.01); *H04N 1/00307* (2013.01); *H04W 88/02* (2013.01); *A61B 5/1172* (2013.01); *H04N 2201/0022* (2013.01)

(58) Field of Classification Search
CPC .. G06K 9/00013; G06K 9/00; G07C 9/00158; H04W 88/02; H04N 1/00307; A61B 5/1172; G06F 21/32; H04L 9/0866; H04L 9/3231; H04L 29/06809; H04L 63/0861; H05K 5/0247; H05K 5/0017; H05K 5/0217; H05K 7/1427; H04M 1/026
See application file for complete search history.

(56) References Cited

U.S. PATENT DOCUMENTS

| | | | | |
|---|---|---|---|---|
| 2002/0050919 | A1* | 5/2002 | Vance | ..................... H01H 13/70 338/47 |
| 2008/0088600 | A1* | 4/2008 | Prest | ................... G06F 3/03547 345/173 |
| 2015/0071509 | A1* | 3/2015 | Myers | .................. G06K 9/0002 382/124 |

(Continued)

*Primary Examiner* — Jeffrey C Pwu
*Assistant Examiner* — Helai Salehi
(74) *Attorney, Agent, or Firm* — Birch, Stewart, Kolasch & Birch, LLP

(57) ABSTRACT

A key module includes a first bracket, a second bracket coupled to the first bracket to form an internal space and including an opening region, and a sensor bracket allowing a fingerprint sensor unit and a press key unit to be mounted therein, and mounted to be movable in the internal space such that one region of the fingerprint sensor unit is exposed through the opening region, wherein one surface of the fingerprint sensor unit is exposed, the press key unit is disposed on the other surface of the fingerprint sensor unit, and the press key unit includes a circuit board and a dome switch disposed on the circuit board to face the first bracket.

12 Claims, 5 Drawing Sheets

(56) References Cited

U.S. PATENT DOCUMENTS

2015/0294135 A1* 10/2015 Kim .................. H01L 23/04
                                                    382/124
2015/0334859 A1* 11/2015 Lee .................. H05K 5/0247
                                                    361/749

* cited by examiner

KEY MODULE AND MOBILE TERMINAL HAVING THE SAME

CROSS-REFERENCE TO RELATED APPLICATION

Pursuant to 35 U.S.C. § 119(a), this application claims the benefit of earlier filing date and right of priority to Korean Application No. 10-2017-0015109, filed on Feb. 2, 2017, the contents of which is incorporated by reference herein in its entirety.

BACKGROUND OF THE INVENTION

1. Field of the Invention

The present disclosure relates to a mobile terminal having a user input module.

2. Background of the Invention

Terminals may generally be classified as mobile (portable) terminals and stationary terminals according to a moveable state. Mobile terminals may also be classified as handheld terminals and vehicle mount terminals according to a user's carriage method.

Terminals have various functions in line with development of technologies. For example, terminals support more complicated functions such as capturing images or video, reproducing music or video files, playing games, receiving broadcast signals, and the like. By comprehensively and collectively implementing such functions, the mobile terminal may be embodied in the form of a multimedia player or a device. In order to support and increase functions of terminals, improvement of structural parts and/or software parts of terminals may be taken into consideration.

Recently, a key module in which a fingerprint sensor and a press key module are integrated is realized. However, after the press key module is installed in a main body of a mobile terminal, a driving state of the press key mode is to be checked by applying an external force. If the press key module is defective, the assembled main body should be disassembled, causing cumbersomeness and loss in cost.

SUMMARY OF THE INVENTION

Therefore, an aspect of the detailed description is to provide a key module which is waterproof and which can be tested in operation before being installed in a terminal body.

To achieve these and other advantages and in accordance with the purpose of this specification, as embodied and broadly described herein, a key module includes a first bracket; a second bracket coupled to the first bracket to form an internal space and including an opening region; and a sensor bracket allowing a fingerprint sensor unit and a press key unit to be mounted therein, and mounted to be movable in the internal space such that one region of the fingerprint sensor unit is exposed through the opening region, wherein one surface of the fingerprint sensor unit is exposed, the press key unit is disposed on the other surface of the fingerprint sensor unit, and the press key unit includes a circuit board and a dome switch disposed on the circuit board to face the first bracket.

In an embodiment, the first region may include an arrest part protruding toward the fingerprint sensor unit, and the fingerprint sensor unit may be formed such that the arrest part is arrested by an outer circumferential surface thereof, and a rubber unit adhered to the second case and the support member such that the sensor bracket is elastically moved may be further provided, whereby the press key unit may be operable within the key module, and thus, it is possible to check an operation of the key module before the key module is fixed to the mobile terminal.

In an embodiment, since the first bracket and the second bracket are adhered to the rear cover or the rear case by a waterproof adhesive member, the inside of the mobile terminal, as well as the inside of the key module, may be waterproof.

According to the present disclosure, since the key module is integrally formed and the press key unit is operable within the key module, an operational state of the press key unit may be checked before the key module is installed in the mobile terminal.

Also, since the press key unit and the second bracket are connected to the elastically deformable rubber unit, although the press key unit is moved, water is not introduced to the inside of the key module due to the presence of the rubber unit. Thus, a waterproof key module may be implemented.

Further scope of applicability of the present application will become more apparent from the detailed description given hereinafter. However, it should be understood that the detailed description and specific examples, while indicating preferred embodiments of the invention, are given by way of illustration only, since various changes and modifications within the scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, digital signage and the like.

Figure 1A:
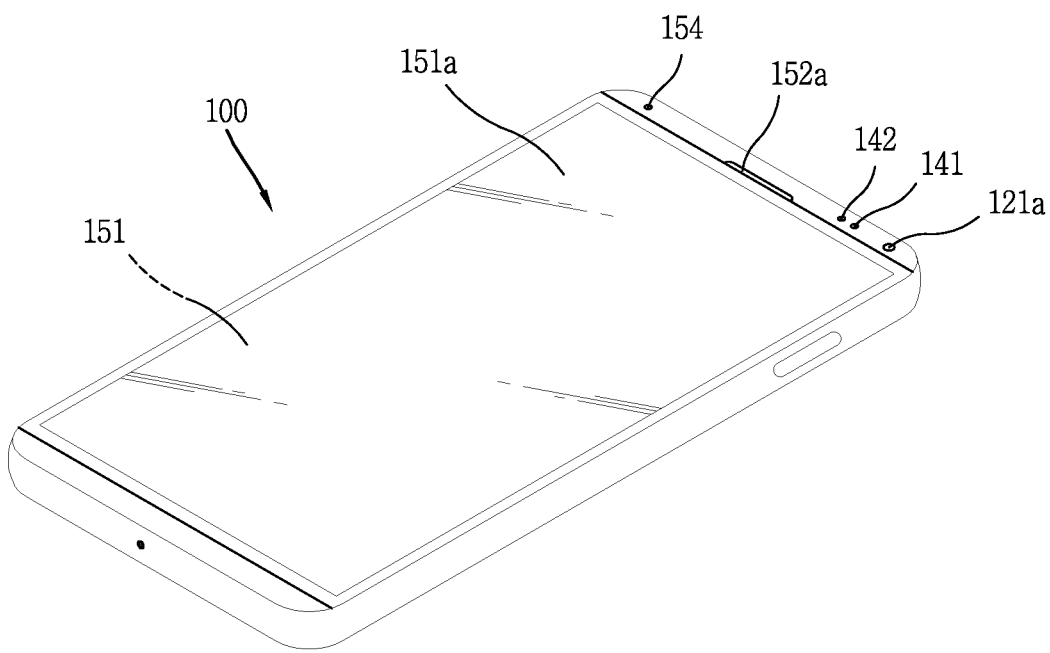
FIGS. 1A and 1B are views of a mobile terminal viewed in different directions according to an embodiment of the present disclosure.
Figure 1B:
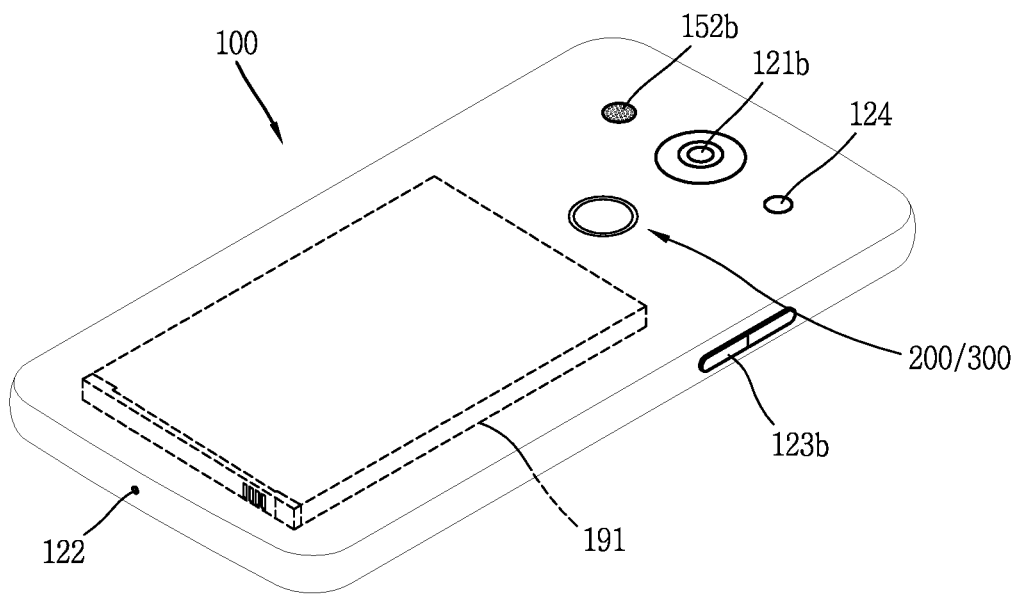

FIGS. 1A and 1B are conceptual views of one example of the mobile terminal, viewed from different directions.

Referring now to FIGS. 1A and 1B, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal 100 may include the display unit 151, the first audio output module 152a, the second audio output module 152b, the proximity sensor 141, the illumination sensor 142, the optical output module 154, the first camera 121a, the second camera 121b, the first manipulation unit 123a, the second manipulation unit 123b, the microphone 122, the interface unit 160, etc.

Hereinafter, the mobile terminal 100 will be explained with reference to FIGS. 1B and 1C. The display unit 151, the first audio output module 152a, the proximity sensor 141, the illumination sensor 142, the optical output module 154, the first camera 121a and the first manipulation unit 123a are arranged on the front surface of the terminal body. The second manipulation unit 123b, the microphone 122 and the interface unit 160 are arranged on the side surfaces of the terminal body. The second audio output module 152b and the second camera 121b are arranged on the rear surface of the terminal body.

However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. For example, the display unit 151 may display information on an execution screen of an application program driven in the mobile terminal 100, or a User Interface (UI) or a Graphic User Interface (GUI) associated with such execution screen information.

The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the control unit 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output unit 152a may be implemented as a receiver for transmitting a call sound to a user's ears, and the second audio output unit 152b may be implemented as a loud speaker for outputting each type of alarm sounds or a play sound of multimedia.

It may be configured such that the sounds generated from the first audio output module 152a are released along an assembly gap between the structural bodies (e.g., between the window 151a and the front case 101). In this case, a hole independently formed to output audio sounds may not be seen or hidden in terms of appearance, thereby further simplifying the appearance of the mobile terminal 100.

The optical output module 154 can output a signal for indicating an event generation using light of a light source. Examples of events generated in the mobile terminal 100 may include message reception, call signal reception, a missed call, an alarm, a schedule notice, an email reception, information reception through an application, and the like. A signal output by the optical output module 154 may be implemented in such a manner that the mobile terminal emits monochromatic light or light with a plurality of colors. The signal output may be terminated as the mobile terminal senses that a user has checked the generated event, for example.

The first camera 121a processes image data of still pictures or video acquired by an image capture device in a video capturing mode or an image capturing mode. The processed image frames may be displayed on the display unit 151, or may be stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may be implemented in a user's non-tactile manner, e.g., by a proximity touch, a hovering touch, etc.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The control unit 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121*b* can include a plurality of lenses arranged along at least one line. The plurality of lenses may also be arranged in a matrix configuration. The cameras may be referred to as an "array camera." When the second camera 121*b* is implemented as an array camera, images may be captured in various manners using the plurality of lenses and images with better qualities.

As shown in FIG. 1C, a flash 124 is shown adjacent to the second camera 121*b*. When an image of a subject is captured with the camera 121*b*, the flash 124 may illuminate the subject.

As shown in FIG. 1B, the second audio output module 152*b* can be located on the terminal body. The second audio output module 152*b* may implement stereophonic sound functions in conjunction with the first audio output module 152*a*, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 (refer to FIG. 1A) may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Referring to FIG. 1B, a key module 200 or 300 including a fingerprint sensor unit is disposed on the rear surface. However, the key module 200 or 300 may also be disposed on the front surface. A fingerprint sensor is disposed on one exposed surface of the key module 200 or 300, and a control command is formed by pressing based on an external force.

Hereinafter, an integrated key module 200 or 300 including the fingerprint sensor unit and a waterproof structure will be described in detail.

Figure 2A:
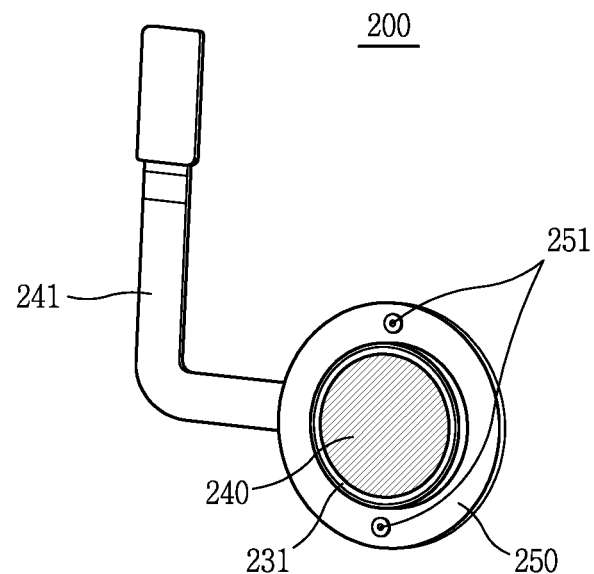
FIG. 2A is a view of a key module according to an embodiment of the present disclosure, viewed in one direction.
Figure 2B:
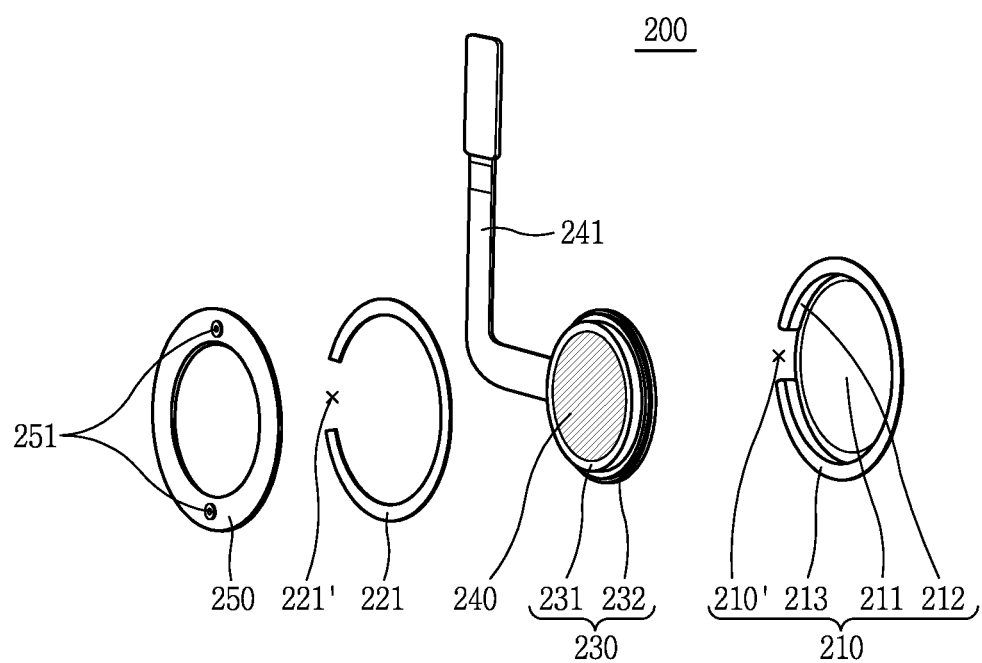
FIG. 2B is an exploded view of the key module of FIG. 2A.

FIG. 2A is a view of a key module according to an embodiment of the present disclosure, viewed in one direction, and FIG. 2B is an exploded view of the key module of FIG. 2A.

Figure 3:
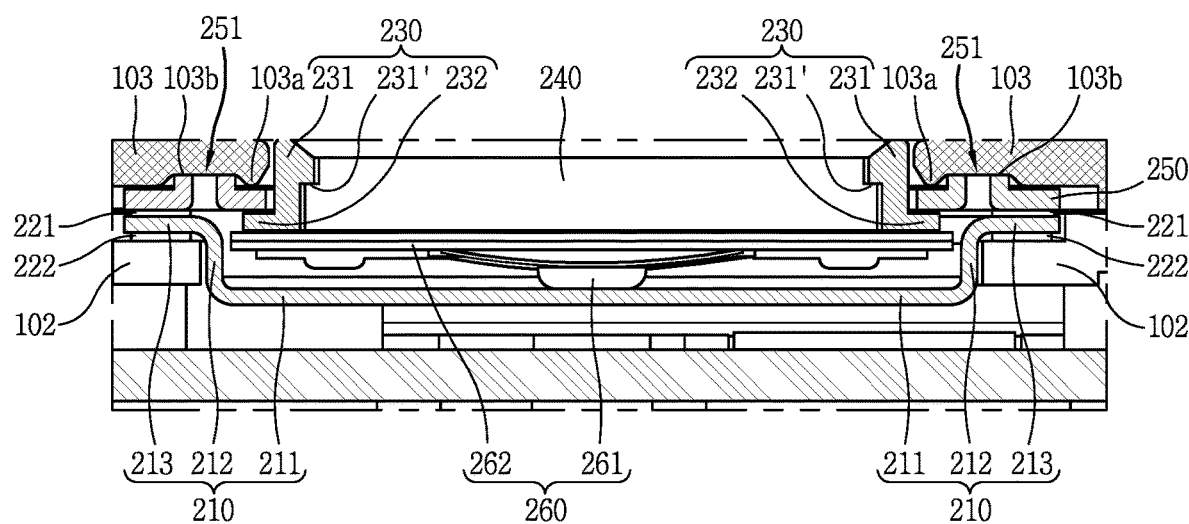
FIG. 3 is a partial cross-sectional view illustrating a state in which the key module of FIG. 2A is installed in a terminal body.

FIG. 3 is a partial cross-sectional view illustrating a state in which the key module of FIG. 2A is installed in a terminal body.

Referring to FIGS. 2A and 3, a key module 200 according to the present embodiment includes a first bracket 210, an adhesive layer 221, a sensor bracket 230, a fingerprint sensor unit 240, a second bracket 250, and a press key unit 260.

The first and second brackets 210 and 250 are assembled to form an internal space. The first bracket 210 includes a support part 211 and a side wall part 212 protruding from edges of the support part 211. The side wall part 212 includes an adhesive part 213 bent in a protruding direction.

A receiving space is formed between the support part 211 and the side wall part 212 by a height of the side wall part 212. The sensor bracket 230 in which fingerprint sensor part 240 and the press key unit 260 are mounted is received in the receiving space.

Meanwhile, the second bracket 211 has a plate shape of an open loop in which an opening region is formed at the center thereof. The sensor bracket 230 penetrates through the opening region such that the fingerprint sensor unit 240 is exposed.

An outer circumference of the second bracket 211 is formed to be substantially same as an outer circumference of the adhesive part 213, and an adhesive layer 221 is formed between the first bracket 211 and the adhesive part 213. The first and second brackets 210 and 250 are integrally fixed by the adhesive layer 221. That is, the adhesive layer 221 is formed on one surface of the adhesive part 213 and the second bracket 250 is adhered to the adhesive layer 221.

Meanwhile, the sensor bracket 230 is exposed to the outside through the opening region, and includes a first region 231 configured to surround the fingerprint sensor unit 240 and a second region whose outer circumference is formed to be greater than the opening region so as to be arrested by the second bracket 250. The first region 231 is disposed in an internal space of the first bracket 210.

The sensor bracket 230 is not separated from the second bracket 250 by the first region 231. The sensor bracket 230 is movable in a state of being arrested by the second bracket 250 and in a state of being received in the first and second brackets 210 and 250 by an external force.

Meanwhile, the first region 231 includes an arrest part 231' protruding toward a center, and the arrest part 231' is arrested by a step part formed on an outer circumferential surface of the fingerprint sensor unit 240. Accordingly, since the fingerprint sensor unit 240 is arrested by and assembled with the first region 231, the fingerprint sensor unit 240 may be prevented from being separated from the sensor bracket 230.

The fingerprint sensor unit 240 is disposed on one surface of the sensor bracket 230, and the press key unit 260 is disposed on the other surface of the sensor bracket 230. The press key unit 260 is supported by the support part 211 of the first bracket 210. The press key unit 260 includes a dome switch 261 and a circuit board 262, and the dome switch 261 includes an externally protruding actuator. The actuator is formed to face the support part 211. That is, when an external force is applied by the sensor bracket 230 or the fingerprint sensing unit 240, the sensor bracket 230 itself moves within the first bracket 210. The dome switch 261 is pressed by the actuator supported by the support part 211, and an electrical signal is generated by the circuit board 262.

A flexible circuit board 241, which serves to transfer the electrical signal and fingerprint information obtained by the fingerprint sensor unit 240 to the main circuit board, extends from the sensor bracket 230. In order to allow the flexible circuit board 241 to extend outwardly, the first bracket 210 includes a recess 210' in which the flexible circuit board 241 is installed. Also, an adhesive layer 211' includes an opening hole 221' to correspond to the recess 210'.

The integrated key module 200 based on the first and second brackets 210 and 250 may be tested for pressing before it is assembled to the mobile terminal. Since the press key unit 260 is supported by the first bracket 210, an operational state of the press key unit 260 may be checked by applying an external force to the sensor bracket 230 or the fingerprint sensing unit 240.

Referring back to FIG. 3, the integrated key module 200 based on the first and second brackets 210 and 250 is installed between the rear case 102 and the rear cover 103 of the mobile terminal 100.

The first bracket 210 is fixed to the rear case 102 and the second bracket 250 is mounted on the rear cover 103.

An adhesive member 222 is formed on the other surface of the adhesive part 213 to adhere the other surface of the adhesive part 213 and the rear case 102.

Meanwhile, in the second bracket 210, a guide protrusion 251 protruding from one surface in contact with the rear cover 103 is formed. The guide protrusion 251 may be provided in plurality, but the number of the guide protrusions 251 is not limited to the illustrated ones. The guide protrusion 251 may include a central hole and the adhesive layer 221 may be formed in a region of the adhesive part 213 not covering the hole.

An arrest protrusion 103a corresponding to the guide protrusion 251 is formed on an inner surface of the rear cover 103. In the rear cover 103, an opening is formed such that at least a region of the sensor bracket 230 equipped with the fingerprint sensor unit 240 is exposed. The arrest protrusion 103a may be formed along the opening in a region adjacent to the opening.

Also, the rear cover 103 further includes a recess region 103b provided in a region adjacent to the arrest protrusion 103a to allow the guide protrusion 251 to be mounted therein. That is, an end portion of the guide protrusion 251 is mounted in the recess region 103b, and the arrest protrusion 103a is arrested by a side surface of the guide protrusion 251.

Accordingly, the integrated key module 200 may be assembled to the rear cover 103 without an additional adhesive member, and the key module 200 is prevented from being moved or separated from the rear cover 103 due to the presence of the arrest protrusion 103a and the recess region 103b.

According to the present disclosure, since the key module integrally includes the fingerprint sensor unit and the press key unit, whether the key module is defective may be tested before the key module is assembled to the terminal body, simplifying the process.

Figure 4A:
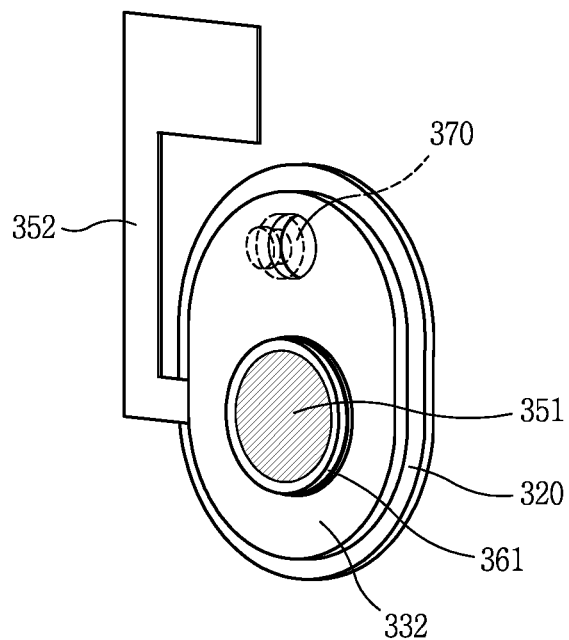
FIG. 4A is a conceptual view illustrating a waterproof key module according to another embodiment of the present disclosure, viewed in one direction.
Figure 4B:
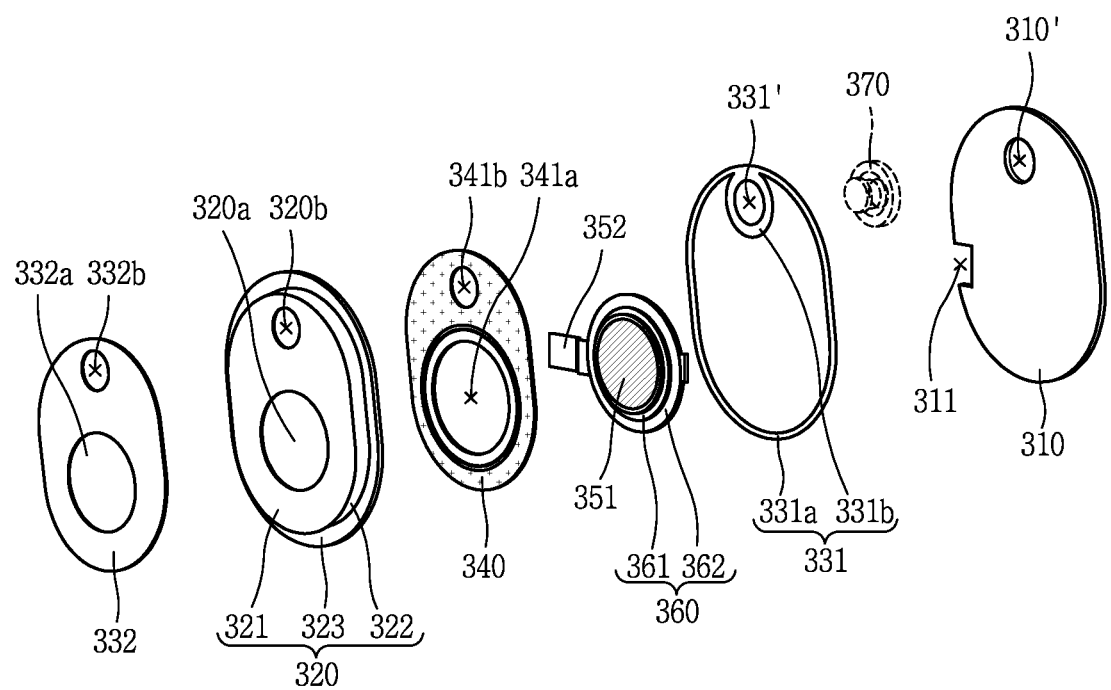
FIG. 4B is an exploded view of the waterproof key module of FIG. 4A.

FIG. 4A is a conceptual view illustrating a waterproof key module according to another embodiment of the present disclosure, viewed in one direction, and FIG. 4B is an exploded view of the waterproof key module of FIG. 4A.

Figure 5A:
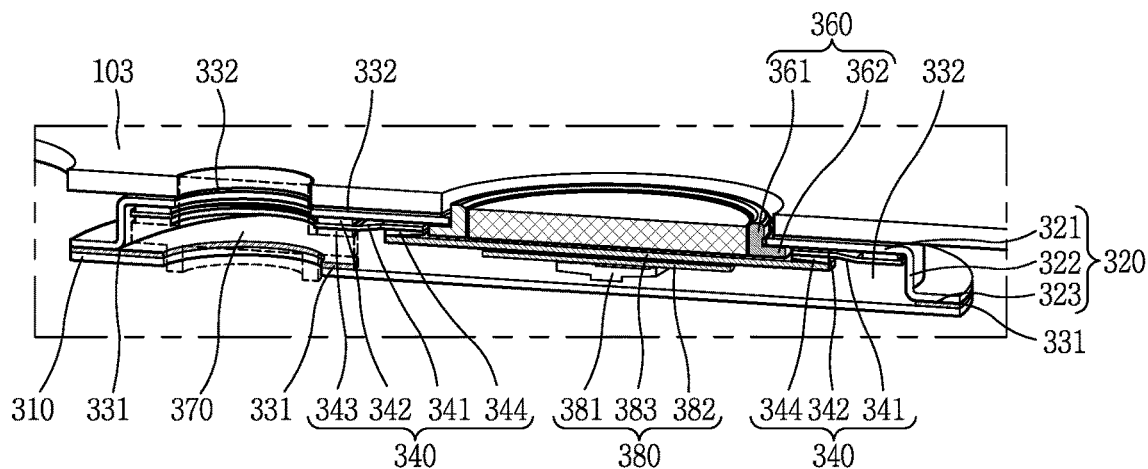
FIG. 5A is a partial cross-sectional view illustrating a state in which the waterproof key module of FIG. 4A is fixed to a rear cover.

FIG. 5A is a partial cross-sectional view illustrating a state in which the waterproof key module of FIG. 4A is fixed to a rear cover.

A key module 300 according to the present embodiment includes first and second brackets 310 and 320, a rubber unit 340, a fingerprint sensor unit 351, a sensor bracket 360, first and second adhesive layers 331 and 332, a press key unit 380, and a flash lens 370. The first and second adhesive layers 331 and 332 are formed as waterproof adhesive members configured to prevent movement of water.

The first and second brackets 310 and 320 are integrally formed to form an internal space by the first adhesive layer 331. The first bracket 310 has a plate shape including a hole 310' corresponding to the flash lens 370.

The second bracket 320 includes a cover region 321 including first and second holes 320a and 320b, a side wall part 322 extending from an edge of the cover region 321 to form an internal space of the second bracket 320, and an adhesive part 333 bent from the side wall part 322 to face the first bracket 310.

The first hole 320a is formed to allow one region of the sensor bracket 360 in which the fingerprint sensor unit 351 is mounted to penetrate therethrough, and the second hole 320b is formed to allow one region of the flash lens 370 to penetrate therethrough.

The first adhesive layer 331 is adhered to one surface of the adhesive part 333 to adhere the first and second brackets 310 and 330. The first adhesive layer 331 includes a first adhesive region 331a formed along the edges of the first and second brackets 310 and 320 to adhere the first and second brackets 310 and 330 and a second adhesive region 331b for adhering the flash lens 370 to the first bracket 310. The second adhesive region 331b is formed along the edge of a cross-section of the flash lens 370 to allow light to pass through the center of the flash lens 370.

Meanwhile, the sensor bracket 360 includes a first region 361 exposed to the outside through the opening region and configured to surround the fingerprint sensor unit 351 and a second region 362 formed to be greater than opening region in an outer circumference so as to be arrested by the second bracket 320. The first region 361 is disposed in an internal space of the first bracket 320.

The sensor bracket 360 may not be separated from the second bracket 320 due to the first region 231. The sensor bracket 360, in a state of being arrested and fixed by the second bracket 250, is movable to a state of being received by the first and second brackets 310 and 320 by an external force.

Meanwhile, although not shown in FIG. 5A, the first region 361 may include an arrest part protruding toward the center. The arrest part may be formed to be arrested by a step part formed on an outer circumferential surface of the fingerprint sensor unit 351 to prevent separation of the sensor bracket 230 and the fingerprint sensor unit 351.

The fingerprint sensor unit 351 is disposed on one surface of the sensor bracket 360, and the press key unit 380 is disposed on the other surface of the sensor bracket 360. The press key unit 380 is supported by the first bracket 310. The press key unit 380 includes a dome switch 381 and a circuit board 382, and the dome switch 381 includes an externally protruding actuator. The circuit board 382 may be formed on the support member 383, and the support member 383 is adhered to the rubber unit 340.

The actuator is formed to face the first bracket 310. That is, when an external force is applied by the sensor bracket 360 or the fingerprint sensor unit 351, the sensor bracket 360 itself moves within the second bracket 320. The dome switch 382 is pressed by the actuator supported by the first bracket 310, and an electrical signal is generated by the circuit board 382.

A flexible circuit board 352, which serves to transfer the electrical signal and fingerprint information obtained by the fingerprint sensor unit 351 to the main circuit board, extends from the sensor bracket 360. In order to allow the flexible circuit board 352 to extend outwardly, the first bracket 310 includes a recess 311 in which the flexible circuit board 352 is installed.

The rubber unit 340 is adhered to an inner surface of the cover region 331 of the first bracket 320. The rubber unit 340 may have the substantially same size at that of the inner surface of the cover region 331 and include first and second holes 341a and 341b corresponding to the first and second holes 320a and 320b.

Referring to FIGS. 4B and 5A, the rubber unit 340 includes a rubber layer 341 and first to third adhesive members 342, 343, and 344. In order to adhere the rubber layer 341 to an inner surface of the cover region 331, the first adhesive member 342 is adhered to an inner surface of the cover region 331.

The second adhesive member 343 is adhered to one surface of the flash lens 370, and the third adhesive member 344 is adhered to the support member 383. The rubber layer 341 is formed of an elastically deformed material, and since the support member 383 is adhered to the rubber layer 341, the sensor bracket 360 including the fingerprint sensor unit 340 and the press key unit 380 may be movable. Also, when the external force is removed due to elastic restoring force of the rubber layer 341, the sensor bracket 360 may be moved to its original position.

Due to the first to third adhesive members 342, 343, and 344, and the rubber layer 341, water, which may be introduced from the first and second holes 320a and 320b of the second bracket 320, does not flow to a space formed by the first and second brackets 310 and 320.

The key module 300 according to the present embodiment is adhered to the rear cover 103 by the second adhesive layer 332. The second adhesive layer 332 is adhered to the cover region 321 of the second bracket 320. The second adhesive layer 332 is formed to be substantially same as the cover region 321 of the second bracket 320 and includes first and second holes 332a and 332b corresponding to the first and second holes 320a and 320b.

Referring to FIG. 5A, water may be introduced to an opening region through which one region of the key module 300 and one region of the flash lens 370 are exposed. However, movement of water flowing through an outer surface of the key module 300 may be prevented by the second adhesive layer 332. Also, water, introduced to an outer circumference of the first region 361, is blocked from moving to a gap between the first and second brackets 310 and 320 by the first to third adhesive members 342, 343, and 344 of the rubber unit 340. Thus, the key module 300 of the present disclosure may be configured to have a waterproof structure blocking an introduction of water.

Thus, an introduction of water to an internal space formed by the first and second brackets 310 and 320 and an external space of the key module 300 may be blocked.

Figure 5B:
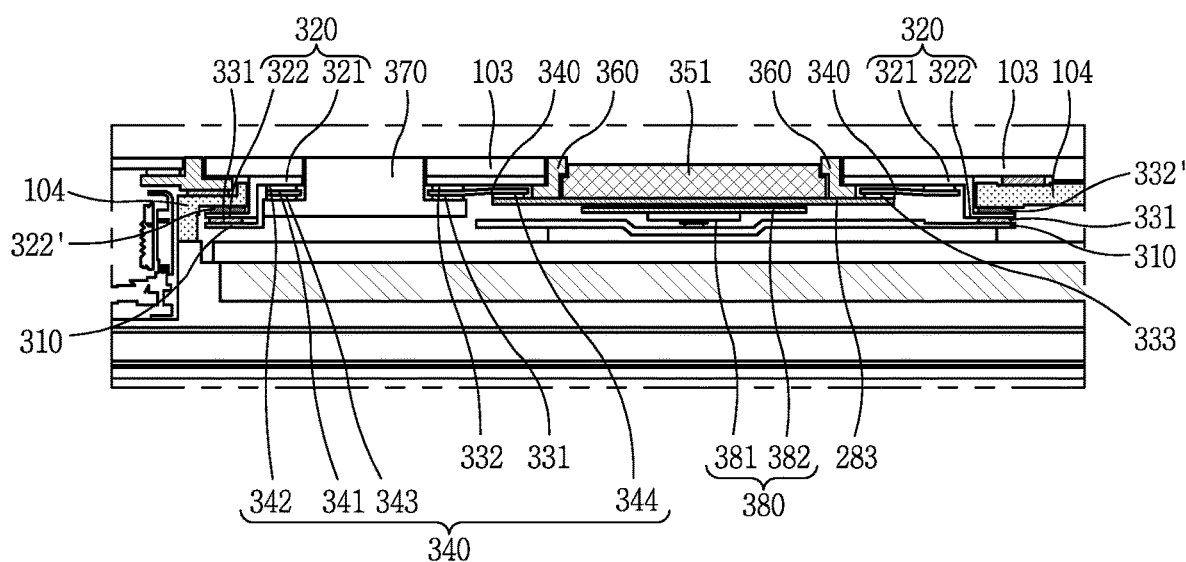
FIG. 5B is a partial cross-sectional view of a mobile terminal in which a key module is installed in a rear case according to another embodiment.

FIG. 5B is a partial cross-sectional view of a mobile terminal in which a key module is installed in a rear case according to another embodiment.

Components of the key module 300 of FIG. 5B are substantially the same as those of the key module 300 of FIG. 5A, except for the second adhesive layer 332. Thus, the like and similar components will be given the same reference numerals and redundant descriptions thereof will be omitted.

An outer surface of the cover region 321 of the second bracket 320 is assembled to be in contact with an inner surface of the rear cover 103. An adhesive layer 322' is formed on an adhesive surface 323 of the second bracket 320, and the adhesive surface 323 is adhered to the rear case 102 by the adhesive layer 322'.

Due to the presence of the adhesive layer 322', movement of water flowing to an internal space of the terminal body, outside of the first and second brackets 310 and 320, may be blocked. Thus, the key module 300 may be waterproof by itself and prevents movement of water to the inside of the terminal body by the adhesive layer adhering the key module 300.

The present invention described above may be implemented as a computer-readable code in a medium in which a program is recorded. The computer-readable medium includes any type of recording device in which data that can be read by a computer system is stored. The computer-readable medium may be, for example, a hard disk drive (HDD), a solid state disk (SSD), a silicon disk drive (SDD), a ROM, a RAM, a CD-ROM, a magnetic tape, a floppy disk, an optical data storage device, and the like. The computer-readable medium also includes implementations in the form of carrier waves (e.g., transmission via the Internet). Also, the computer may include the controller 180 of the terminal. Thus, the foregoing detailed description should not be interpreted limitedly in every aspect and should be considered to be illustrative. The scope of the present invention should be determined by reasonable interpretations of the attached claims and every modification within the equivalent range are included in the scope of the present invention.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. A key module comprising:
    a first bracket, comprising:
        a support region supporting a dome switch;
        a side wall part extending along an edge of the support region to form an internal space; and
        an adhesive part having one surface adhered to a second bracket, wherein the second bracket is coupled to the first bracket to form the internal space and includes an opening region;
    a sensor bracket allowing a fingerprint sensor unit and a press key unit to be mounted therein, and mounted to be movable in the internal space such that one region of the fingerprint sensor unit is exposed through the opening region; and
    an adhesive layer formed along edges of the first and second brackets to couple the first and second brackets, wherein:
    one surface of the fingerprint sensor unit is exposed,
    the press key unit is disposed on the other surface of the fingerprint sensor unit,
    the press key unit includes a circuit board and the dome switch, the dome switch being disposed on the circuit board to face the first bracket, an outer circumference of the second bracket is formed to be the same as an outer circumference of the adhesive part, and the first bracket and the second bracket are integrally fixed by the adhesive layer.

2. The key module of claim 1, wherein the sensor bracket includes:

a first region surrounding the fingerprint sensor unit; and a second region formed to be greater than the opening region in an outer circumference and arrested by the second bracket.

3. The key module of claim 1, further comprising:

a support member fixed to a lower end of the fingerprint sensor unit and the sensor bracket; and a rubber unit adhered to the second case and the support member such that the sensor bracket is elastically moved.

4. The key module of claim 2, wherein the first region includes an arrest part protruding toward the fingerprint sensor unit, and the fingerprint sensor unit includes a step part formed on an outer circumferential surface such that the arrest part is arrested by the step part.

5. The key module of claim 3, wherein the rubber unit includes:

a rubber layer configured to be elastically deformable;

a first adhesive member adhering one surface of the rubber layer and the second bracket; and a second adhesive member adhering the other surface of the rubber layer and the support member.

6. The key module of claim 5, further comprising:

a flash lens, wherein the second bracket further includes an additional opening region through which one region of the flash lens penetrates, and the rubber unit further includes a third adhesive member adhering the flash lens and the rubber layer.

7. A mobile terminal comprising:

a terminal body including a front case, a rear case, and a rear cover coupled to the rear case;

a key module disposed between the rear cover and the rear case, wherein the key module includes:

a first bracket, comprising:

a support region supporting a dome switch;

a side wall part extending along an edge of the support region to form an internal space; and an adhesive part having one surface adhered to a second bracket, wherein the second bracket is coupled to the first bracket to form the internal space and includes an opening region;

an adhesive layer formed along edges of the first and second brackets to couple the first and second brackets; and a sensor bracket allowing a fingerprint sensor unit and a press key unit to be mounted therein, and mounted to be movable in the internal space such that one region of the fingerprint sensor unit is exposed through the opening region, wherein:

one surface of the fingerprint sensor unit is exposed, the press key unit is disposed on the other surface of the fingerprint sensor unit, the press key unit includes a circuit board and the dome switch is disposed on the circuit board to face the first bracket, an outer circumference of the second bracket is formed to be the same as an outer circumference of the adhesive part, and the first bracket and the second bracket are integrally fixed by the adhesive layer.

8. The mobile terminal of claim 7, wherein the second bracket includes a plurality of guide protrusions protruding from one surface of the second bracket facing the rear cover, and the rear cover includes an arrest protrusion formed to be arrested by the plurality of guide protrusions.

9. The mobile terminal of claim 7, wherein the other surface of the adhesive part is fixed to the rear surface.

10. The mobile terminal of claim 7, wherein the second bracket includes:

a cover region in which the opening region is formed;

a side wall part extending from the cover region and forming the internal space; and an adhesive part having one surface adhered to the first bracket.

11. The mobile terminal of claim 10, wherein the adhesive layer is further adhered the rear cover and the cover region, and wherein the adhesive layer is configured as a waterproof adhesive member.

12. The mobile terminal of claim 10, further comprising:

wherein the adhesive layer is formed on an other surface of the adhesive part and adheres the second bracket and the rear case, and wherein the adhesive layer is configured as a waterproof adhesive member.

* * * * *